Figure 1:
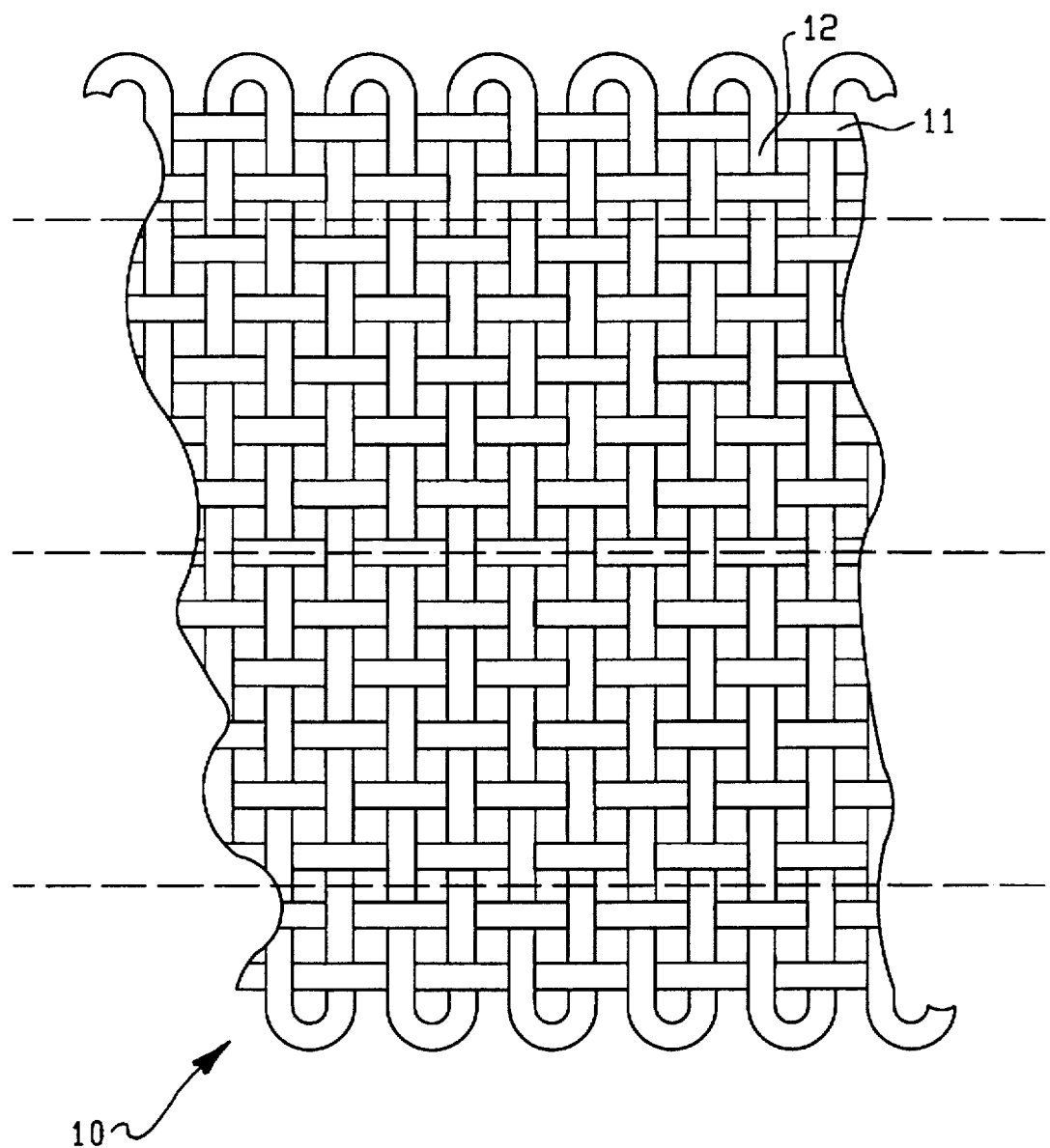

United States Patent
Borer

Patent Number: 5,786,283
Date of Patent: Jul. 28, 1998

[54] DENTAL REINFORCEMENT STRIP

[76] Inventor: Geri Borer, Pilatusstrasse, Lucerne, Switzerland, 6003

[21] Appl. No.: 600,784

[22] Filed: Feb. 13, 1996

[30] Foreign Application Priority Data

Feb. 14, 1995 [CH] Switzerland .................. 00 430/95

[51] Int. Cl.$^6$ .................................................. D05B 93/00
[52] U.S. Cl. ..................... 442/186; 112/402; 112/412; 139/383 R; 139/426 R; 442/239; 442/240; 442/241
[58] Field of Search .................. 442/186, 239, 442/240, 241; 112/402, 412; 139/383 R, 426 R

[56] References Cited

U.S. PATENT DOCUMENTS 4,384,854  5/1983  Garfinhel .................. 433/215
5,176,951  1/1993  Rudo .......................... 428/229

*Primary Examiner*—James J. Bell

[57] ABSTRACT

A strip for dental plastic retainers or plastic dental prosthesis consisting of at least 4 and at most 8 interconnected layers of endless threads which possess a yarn count of less than 1 tex; the strip possesses a thickness of maximum 500 μm; the endless fibers of a layer (10) consist preferably of colorless glass fibers in which the cross linkage of the resin which beds-in the fibers is simplified by the effects of light. Preferably, each individual layer consists of a strip whose warp threads (11) and weft yarns (12) are combined to a woven strip in the form of a plain fabric weave bond.

20 Claims, 1 Drawing Sheet

DENTAL REINFORCEMENT STRIP

In the practice of dentistry it is common to use reinforced plastic retainers which can be prefabricated or formed in the mouth of the patient for retaining teeth. As reinforcing material for this purpose there is proposed in U.S. Pat. No. 4,384,854 the use of wire nets and in U.S. Pat. No. 5,176,951 textures of synthetic polymers, namely Aramides, which are known under the registered trade name Kevlar.

The researches for the present invention have shown that glass fibers, against the expectations, are also suitable for dental applications as reinforcing materials if it is possible to make the reinforcing sufficiently compact or tight and yet sufficiently thin in order that it is not found to be uncomfortably disturbing in the mouth of the person wearing it. It is the object of this invention to offer a reinforcing which complies with these requirements.

According to the invention, this object is achieved by means of an insertion strip, hereafter called "strip" for short, which is suitable for plastic dental retainers or for plastic dental prosthesis and characterized in that it consists of at least 4 and at most 8 interconnected layers of endless threads which possess a yarn count of less than 1 tex and in which the strip possesses a thickness of maximum 500 µm.

As "endless threads" there are designated here, individual, therefor not necessarily filaments which are gathered together in one rope, thread or ply which practically possesses any particular length as is typical for threads which are spun from a melt or solution. Generally, for this invention, there are preferred filaments from common clear and uncolored mineral glass, for example, the glass types designated E-glass without further additives besides the spinning additives. Basically, however, other non-metallic inorganic materials can also be used, preferably those suitable for actinic radiation such as transparency to light, for example, filaments of quartz or other ceramic oxides insofar as they can be spun to the corresponding fineness as filaments. The material of the filaments should, in any case, correspond to the general requirements for applications in the mouth cavity, and be especially free from health or toxicological suspect components.

Preferred filaments of glass have a yarn count of 0.1–0.5 dtex (decitex) and a thickness of maximum 10 µm, e.g. 4–6 µm. The filaments are preferably combined to ropes or threads of 50–150 filaments, and two or more threads can be combined to a single yarn. In each case it is important that the layers of the strip lying on each other together posses a maximum thickness of 0.5 mm.

For many purposes of application it is preferred that the bundle of filaments or ropes are combined together to a flat form, e.g. a fabric with plain fabric binding. Also filament bands in form of hosiery or mesh can be suitable if they are obtainable in a correspondingly thin form.

The filaments, or strips can be provided with the usual sizing which, if desired, can be removed before contact with the cross-linkable polymer; however this is not desirable as a rule.

The strip, according to the invention, consists of at least 4 and a maximum of 8 combined layers. The layers can be formed by means of repeated folding of a correspondingly wide starting strip or by means of binding several individual layers placed on top of each other. However, the folding of relatively wider strips is less preferred due to the breaking tendency of inorganic, non-metallic and especially filaments consisting of glass. Therefor, sharp folds in the filaments at the edge or in the region of the borders should be avoided wherever possible. It is advisable for each part strip of a layer to possess a woven edge.

The interconnected layers of the strip can, for example, each consist of several woven ropes, yarns or ply yarns of endless filaments e.g. woven in a plain fabric binding each possessing a thickness of 40–80 µm. The total strip as a rule has a width of 2 to 8 mm.

The layers of the strip can be connected to each other by means Qf sewing or other method, e.g. by means of gluing. Generally, it should be taken into account that the strip and all its components with the cross linked polymer which is used for the retainer or dental prosthesis are also compatible with the requirements, for the cross linking. Preferred cross-linkable polymers, for example, are those which permit themselves to be cross linked by the effects of actinic radiation, e.g. light. Suitable polymer preparations, for example, on the basis of (Meth) Acryl-Polymers, including the usual cross linking media or catalyzers are well known to a person well versed in the profession and technically available.

In fact, the basis of one of the advantages of a strip of glass fiber according to the invention over the known metal wire sieves lies in that the glass fibers are well transparent to light.

The invention includes a procedure for the creation of dental plastic retainers or plastic dental prosthesis with the combination of a cross-linkable polymer mass with a reinforcement of endless fibers and subsequent cross linking, which means polymerization of the polymer mass up to a duroplastic condition.

The procedure can be carried out outside or inside the mouth cavity of the patient. According to a preferred method, plastic retainers are formed for optimal fitting in the mouth of the patient and cross linked. According to the invention, there is used in this for reinforcement a strip which consists of at least 4 and at most 8 interconnected layers of endless threads which each possess a yarn count of less than 1 tex and in which the strip possesses a thickness of maximum 500 µm. Preferred forms of execution of the procedure utilize strips with the mentioned preferred characteristics.

The accompanying single FIG. 1 shows a schematic plan view on a layer 10 of a strip according to the invention. The layer 10 is a strip of glass fiber woven in a plain fabric binding which form the warp threads 11 as well as the weft yarns 12. Four to eight layers 10, e.g. in the form of individual strips placed on top of each other, are interconnected, for example, by means of a single longitudinal center seam B1, by means of 2 longitudinal outer seams B2, B3 or by means of three or more parallel longitudinal seams B1, B2, B3. Instead of the sewn seam lines, other connection lines could also be utilized, for example in the form of adhesive lines or adhesive surfaces (not shown). It must be mentioned that each warp thread 11 and each weft yarn 12 always consists of numerous filaments. Typically, about twice as many monofilaments are used for the warp threads 11 as for the weft yarn 12, e.g. about 200 filaments for the warp and 100 filaments for the weft yarn.

The plain fabric binding is preferred for the strips 10 of the individual-layers of the multi-layer strips according to the invention, but this is not critical and can be replaced by other forms of weave, for instance weft twill or weft satin.

The invention is further detailed in the following examples. All numerical information with "about" include an error limit of ±20%.

APPLICATION 1

Manufacture of the Multi-Layer Strip for the manufacture of a multi-layer strip, a commercially obtainable technical glass fiber strip with the following specifications was utilized.

Width: about 4 mm;

Weight: about 220 g/km or 55 g/m2;

Thickness: about 0.06 mm.

Plain fabric binding, conventional manufacture on a shuttle loom. Glass filaments of E-glass with 0.55 dtex;

Filament diameter: 5 μm;

Warp: 15 parallel filament ropes of each about 200 filaments,

Weft: 18 weft ropes of each about 100 filaments /cm strip length.

Threads of E-glass, each thread from each a yarn consisting of about 100 filaments, 5.5 tex×1.

For spinning, the fibers were treated with commercially available size (e.g. Dexol, registered trade mark of Isover SA, Lausanne, Switzerland).

Six layers of this glass fiber strip were sewn together by means of a single seam situated near the middle. The sewing medium used can be a glass filament ply yarn, for instance such a one as in the warp-or a ply yarn of another material.

The sewn-together 6 layer strip was wound into a roll of about 6 cm diameter and stored in this form until its application.

APPLICATION 2

Creation of a Plastic Retainer for Blocking

For blocking loose teeth by means of a glass fiber reinforced plastic retainer, called a "fiber splint" for short in the following, the following method of working was carried out:

a) Tooth preparation: An impression of conventional elasticized impression material is taken of the teeth to be retained. As the impression is subsequently to be utilized as "key" for the adaptation of the fiber splint, it is shortened lingually approximately at the height of the gingiva and facially slightly below the cutting edges. The interdental septals are shortened on the lingual side. A cofferdam is placed over the teeth to be treated and the teeth are cleaned as for the etching technique. The enamel of the teeth to be retained are etched on the oral side and the interdentally sides.

b) A piece of the multi-layer strip of Application 1, the length corresponding to the teeth to be retained, is cut off. The oral and interdental surfaces of the teeth are painted with the thinnest possible layer of a commercially available tooth bonding liquid, a medium of light-hardening fluid polymer mass on an acrylic base, and the bonding layer blown over with a weak blast of air. Now the multi-layer strip is soaked outside the mouth cavity with the bonding fluid and is now ready to be utilized as a retainer.

c) The Retainer is placed on the oral enamel surfaces, the retainer is adapted with the key derived from the impression and lightly pressed on to the teeth. The bonding agent is linked to the facial and oral side with the light polymerization device. If desired, several layers of the 6-layer strip can be applied. The key impression, of transparent material, is used as a mould for the exact adaptation of the strip d) The retainer formed in this manner can be worked with the bonding agent and is then veneered and polished like a composite filling. Finally, the cofferdam is removed, the occlusion is controlled and ground in as required.

APPLICATION 3

Regluing Extracted Teeth a. First an impression is made of the teeth to be treated as in Application 2. Then the course of the gingiva is drawn on the tooth to be extracted, e.g. with a waterproof felt tipped pen. The tooth is then removed under anesthetic taking care not to damage the gingiva. The tooth is shortened 1–2 mm at the apical side of the marking and the interface is veneered. Then the pulp canal is closed and a cofferdam is placed over the remaining teeth.

b. The teeth, including the extracted tooth, are cleaned as in Application 2 and etched. The extracted tooth is reset by means of the key and provisionally fixed to the neighboring teeth by means of a little bonding agent.

c. The oral and interdental surfaces are painted with a fine layer of bonding agent and lightly air blown with a weak stream of air.

d. A plastic retainer is formed after the method of working described in paragraph b of Application 1; it is placed on the oral enamel surface and adapted with the key or lightly pressed on and finally linked with the light polymerization device. The bridge formed in this way is veneered as described in the previous Application.

APPLICATION 4

Inserting Totally Dislocated Teeth a. The teeth, including the crown of the dislocated tooth are cleaned and etched as described above. After anesthesia, the dislocated tooth is reset and the teeth to be treated are etched on the oral side and the interdental.

b. As in the previous Applications, an impression using a transparent elasticized polymer material is made of the teeth to be treated and shortened for use as a key.

c. The retainer is manufactured as described in Application 1 paragraph b and, after insertion of the key, polymerized by means of light. If required in this case, the retainer can also be applied facially.

APPLICATION 5

Manufacture of Reinforced Bridges in the Dental Laboratory a. First a diagnostic model (so-called wax-up) is created and cast with elasticized mass. The abutment teeth are ground and fundamentally isolated.

b. the multilayer strip is cut to double the length of the bridge with an addition of 20 length % and soaked with a duroplastic polymarisable bonding agent. Then the strip is placed approximately in its center about the distal abutment tooth and adapted with clips in the interdental cavities as well as mesial and distal of the abutment teeth.

c. After polymerization, the clips are removed. Now a further piece of multi-layer strip is placed on the occlusion surface and linked by means of the bonding agent which can be duroplastically polymerized under the influence of light.

d. The scaffolding achieved in this way is removed from the abutment teeth, reworked and reset. The key is tested on the model, and then filled with conventional crown bridge plastic and reset in the usual manner on the model. After the cross linkage, the key is removed, the bridge is removed from the model and processed in the normal manner.

APPLICATION 6

Creation of a Reinforced Bridge in the Mouth of the Patient a. A key of elasticized material is created as described in Application 1 and after preparation is filled up to about half height with the usual provisional plastic.

b. One or two layers of the multi-layer strip with about the length of the bridge on a mixing pad are both soaked simultaneously with bonding agent. The soaked material is then placed into the still-liquid plastic in the key, the key is filled to its full height with plastic and reset in the normal manner. After the cross linkage, the (provisional) bridge is processed in the usual manner.

It must be mentioned that the above Applications serve only as an explanation of the invention and are not to be understood as being limited therein. Generally, all dental work in which reinforcing of a dental plastic form is necessary or required can be carried out with the multi-layered strip. In all such cases a substantial increase in strength is achieved without a significant sacrifice in elasticity.

I claim:

1. Strip for dental plastic retainers characterized in that it consists of at least 4 and at most 8 interconnected layers of endless threads which possess a yarn count of less than 1 tex and in which the strip possesses a thickness of maximum 500 μm.

2. Strip in accordance with claim 1 characterized in that it consists essentially of non-metallic, inorganic and substantially non-water-soluble endless threads.

3. Strip in accordance with claim 2 characterized in that the layers of the strip each consist of several woven ropes of endless filaments.

4. Strip in accordance with claim 1 characterized in that the layers of the strip are connected with each other by sewing.

5. Strip in accordance with claim 1 characterized in that the layers of the strip each consist of several woven ropes of endless filaments.

6. Strip in accordance with claim 2 characterized in that the layers of the strip are connected with each other by sewing.

7. Strip in accordance with claim 3 characterized in that the layers of the strip are connected with each other by sewing.

8. Strip in accordance with claim 1 wherein the endless threads are mineral glass fibers.

9. Strip in accordance with claim 1 wherein the endless threads possess a yarn count of 0.1 to 0.5 dtex and a thickness of no more than 10 μm.

10. Strip in accordance with claim 1 wherein the strip has a width of 2 to 8 mm.

11. Strip in accordance with claim 3 wherein each of the ropes of endless filaments has a thickness of 40–80 μm.

12. Strip in accordance with claim 5 wherein each of the ropes of endless filaments has a thickness of 40–80 μm.

13. Strip in accordance with claim 1 wherein the layers of the strip are glued together.

14. A process for the manufacture of plastic dental retainers and plastic dental prostheses comprising the steps of providing a cross-linkable polymer mass with a reinforcement strip which consists of at least 4 and at most 8 connected layers of endless threads which possess a yarn count of less than 1 tex and in which the strip possesses a thickness of no more than 500 microns; and cross-linking the polymer mass.

15. The process of claim 14 further comprising the step of connecting the layers of the strip by sewing them together.

16. Process in accordance with claim 14 characterized in that the strip consists essentially of hydrophile and substantially non-water-soluble endless threads.

17. Process in accordance with claim 16 characterized in that the layers of the strip each consist of several woven ropes of endless filaments.

18. Process in accordance with claim 14 characterized in that the layers of the strip each consist of several woven ropes of endless filaments.

19. A process for the creation of plastic dental retainers and plastic dental prostheses comprising the steps of providing inside the mouth of the patient a cross-linkable polymer mass with a reinforcement strip which consists of at least 4 and at most 8 connected layers of endless threads which possess a yarn count of less than 1 tex and in which the strip possesses a thickness of no more than 500 microns; and cross-linking the polymer mass.

20. The process of claim 19 further comprising the step of connecting the layers of the strip by sewing them together.

* * * * *

UNITED STATES PATENT AND TRADEMARK OFFICE
CERTIFICATE OF CORRECTION

PATENT NO. : 5,786,283

DATED : Jul. 28, 1998

INVENTOR(S) : Geri Borer

It is certified that error appears in the above-identified patent and that said Letters Patent is hereby corrected as shown below:

On the first page of the patent, after the name of the inventor, please insert therefor -- [73] Assignee: Polydentia S.A., Mezzovico, Switzerland--

Signed and Sealed this

Twenty-eighth Day of September, 1999

Attest:

Q. TODD DICKINSON

*Attesting Officer*    *Acting Commissioner of Patents and Trademarks*